United States Patent [19]
Cashin et al.

[11] Patent Number: 5,756,082
[45] Date of Patent: May 26, 1998

[54] COSMETIC STICK COMPOSITIONS CONTAINING DI—AND TRIBLOCK COPOLYMERS

[75] Inventors: Christopher James Cashin, Dunellen; Fred Nick Hubner, East Brunswick, both of N.J.

[73] Assignee: Revlon Consumer Products Corporation, New York, N.Y.

[21] Appl. No.: 664,091

[22] Filed: Jun. 12, 1996

Related U.S. Application Data

[63] Continuation of Ser. No. 405,473, Mar. 16, 1995, abandoned.

[51] Int. Cl.[6] .............................. A61K 7/00; A61K 7/32
[52] U.S. Cl. .................... 424/78.03; 424/65; 424/66; 424/68; 424/DIG. 5
[58] Field of Search ............................. 424/401, 78.03, 424/DIG. 5, 45, 46, 68

[56] References Cited

U.S. PATENT DOCUMENTS

| | | | |
|---|---|---|---|
| 5,169,626 | 12/1992 | Tanner et al. | 424/66 |
| 5,221,534 | 6/1993 | DesLauriers et al. | 424/78.03 |
| 5,254,332 | 10/1993 | Grezcyn | 424/66 |
| 5,302,381 | 4/1994 | Greczyn | 424/66 |

*Primary Examiner*—Sally Gardner-Lane
*Attorney, Agent, or Firm*—Julie Blackburn

[57] ABSTRACT

A cosmetic stick composition comprising:
a) 5–60% of a volatile silicone,
b) 3–25% of a solidifying agent, and
c) 10–40% of a gel composition comprised of a hydrocarbon oil contained within a polymer network formed by a synthetic diblock copolymer, a triblock copolymer, or mixtures thereof.

16 Claims, No Drawings

COSMETIC STICK COMPOSITIONS CONTAINING DI— AND TRIBLOCK COPOLYMERS

This is a continuation of application Ser. No. 405,473, filed Mar. 16, 1995 now abandoned.

TECHNICAL FIELD

The invention is in the field of cosmetic stick compositions.

BACKGROUND OF THE INVENTION

The invention related to cosmetic sticks, particularly antiperspirant or deodorant cosmetic sticks. Many different types of antiperspirant and deodorant compositions have been described in the literature. Antiperspirant solid stick compositions generally comprise an astringent antiperspirant salt, low and high melting point waxes, and a volatile silicone along with an appropriate gelling agent which will provide a stick with the appropriate consistency. Soap, or sodium stearate, is one well known gelling agent. Soaps have certain disadvantages. In particular they tend to leave a residue on skin and clothes which makes them less than desireable, and they cannot be used with antiperspirant salts. Other gelling agents such as sorbitol derivatives work well except that they are expensive, and give sticks tacky or sticky. Accordingly, there is a need for new cosmetic stick compositions which exhibit improved stick consistency, less residue, and excellent aesthetics.

SUMMARY OF THE INVENTION

A cosmetic stick composition comprising:
a) 5–60% of a volatile silicone,
b) 3–25% of a solidifying agent, and
c) 10–40% of a gel composition comprised of a hydrocarbon oil contained within a polymer network formed by a synthetic diblock copolymer, a triblock copolymer, or mixtures thereof.

DETAILED DESCRIPTION

The cosmetic stick composition of the invention is a low residue stick form. If the cosmetic stick is an antiperspirant, it is preferably a suspensoid stick form, meaning that the antiperspirant salts are suspended within the stick matrix rather than dissolved in water and being emulsified in the stick matrix. The stick may be a solid stick or soft solid stick.

THE VOLATILE SILICONE

The volatile silicone material may be either a linear or cyclic volatile polydimethylsiloxane and is present from 5–60%, preferably 10–50% by weight of the total composition. Cyclic polydimethylsiloxanes have 2 to 7 silicon atoms, and are of the general formula:

$$[\underset{\underset{CH_3}{|}}{\overset{\overset{CH_3}{|}}{Si}}-O]n$$

wherein n=2–7. The cyclic silicones generally have viscosities of less than 10 centistokes at 25° C. The term "volatile" means that the silicone has a measurable vapor pressure. Volatile cyclic silicones of this description are generally referred to as hexamethyl disiloxane, octamethylcyclotetrasiloxane ($D_4$), decamethylcyclopentasiloxane ($D_5$), etc.

The linear polydimethylsiloxanes contain from about 0 to 9 silicon atoms and have the general formula:

$(CH_3)_3Si{-}O[Si(CH_3)2{-}O]_n{-}Si(CH_3)_3$ where n=1–7. The linear volatile silicones generally have viscosities of less than about 5 centistokes at 25° C.

Silicones fitting the above description are commercially available from Dow Corning Corporation under the tradenames Dow Corning 344, 345, 200, 244, and 245 fluids, Union Carbide under the tradenames Silicone 7207 and Silicone 7158, and Stauffer Chemical under the tradenames SWS-03314.

THE SOLIDIFYING AGENT

The solidifying agent must be effective to solidify the composition, which means that it will cause a semi-solid or solid to be formed at room temperature. Waxes are suitable solidifying agents. High melting point waxes, which have a melting point ranging from 65°–110° C. are good solifying agents. Waxes falling into this category include hydrogenated castor oil, paraffin, synthetic wax, ceresin, beeswax, spermaceti, carnauba, candelilla, montan wax, and other Fisher Tropsch waxes such as microcrystalline waxes and mixtures thereof. Low melting point waxes, which have a melting point of 37° to 65° C. are also good solidifying agents. Such waxes include fatty alcohols, fatty acids, fatty acid esters, and fatty acid amides having fatty chains from 8 to 30 carbons, and mixtures thereof. The compositions of the invention contain 3–25%, preferably 3–15% of a solidifying agent.

THE GEL COMPOSITION

The composition comprises 10–40%, preferably 15–30% of a gel composition contained within a polymer network formed by a synthetic diblock copolymer, a triblock copolymer, or mixtures thereof. Such gel compositions are disclosed and claimed in U.S. Pat. No. 5,221,534 which is hereby incorporated by reference. Such gel compositions can be purchased from Penreco, a division of Pennzoil Products Company, and are sold under the tradename Geahlene. The gel composition comprises a hydrocarbon oil and a blend of polymers, said blend of polymers being selected from the group consisting of at least two of a diblock copolymer, a triblock copolymer, a radial polymer, a multiblock polymer, and mixtures thereof, wherein said blend of polymers contains at least one diblock or triblock copolymer. Preferably, the gel compositions comprises 80–99% mineral oil contained within a polymer blend comprised of 1–20% of a mixture of di- and triblock copolymers. Most preferably, the gel composition comprises mineral oil and hydrogenated butylene/ethylene/styrene copolymer and hydrogenated ethylene/propylene/styrene copolymer.

OTHER INGREDIENTS

The cosmetic stick compositions of the invention are preferably used as antiperspirant or deodorant stick compositions. If antiperspirant sticks, they will generally contain 5–35%, preferably 10–30%, more preferably 20–25% astringent antiperspirant salt. The antiperspirant material has particle sizes ranging from 1 to 200, preferably 1–100 microns, and include a variety of aluminum or zirconium astringent salts or complexes well known in the art. The composition of antiperspirant salts is controlled by the Food and Drug Administration, and those approved for use include aluminum or aluminum zirconium salts or complexes such as aluminum chlorde, aluminum chlorohydrate, aluminum chlorohydrex PEG, aluminum chlorohydrex PG, aluminum dichlorohydrate, aluminum dichlorohydrex PEG, aluminum dichlorohydrex PG, aluminum sesquichlorohydreate, aluminum sesquichlorohydrex PEG, aluminum sesquichlorohydrex PG, aluminum sulfate, aluminum zirconium octachlorohydrate, aluminum zirconium octachlorohydrex GLY, aluminum zirconium tetrachlorohydrate, aluminum zirconium trichlorohydrate, aluminum zirconium tetrachlorohydrate GLY, aluminum zirconium tetrachlorohydrate GLY, aluminum zirconium trichlorohydrate GLY, and so on. These antiperspirant salts are also disclosed in the CTFA Cosmetic Ingredient Handbook, Second Edition, 1992, pages 541 to 542, which is hereby incorporated by reference. If the cosmetic stick of the invention is a deodorant stick, generally 0.01–5%, preferably 0.1–2% of a deodorant active compound is present. Deodorant agents are ingredients which reduce or eliminate unpleasant odor and protect against the formation of malodor on body surfaces. Suitable deodorant materials are set forth on page 555 of the CTFA Cosmetic Ingredient Handbook, Second Edition, 1992, which is hereby incorporated by reference. Such deodorant agents include fragrances, bacteriostatic quaternary ammonium compounds such as cetyl-trimethyl ammonium bromide, cetyl pyridinium chloride, benzethonium chloride, diisobutyl phenoxy ethoxy ethyl dimethyl benzyl ammonium chloride, sodium N-lauryl sarcosine, sodium N-polymethyl sarcosine, lauroyl sarcosine, N-myristoyl glycine, potassium N-lauroyl sarcosine, stearyl trimethyl ammonium chloride, and mixtures thereof. Other suitable deodorant materials include 2,5,5'-tri-chloro-2'-hydroxydiphenyl ether, or Triclosan, sodium bicarbonate, 3,7,11,-trimethyldodeca-2,6, 10-trienol which is a bacteriostatic agent known by the tradename FARNESOL, and the like.

The composition of the invention may also comprise 5–45%, preferably 10–40% particulate materials other than the antiperspirant active. Suitable particulate materials should be inert, generally have particle sizes of about 15–300 microns, are water insoluble, and which do not melt, decompose, or react with the wax, silicones, or other ingredients present. Suggested particulates include polyolefins, particularly polyethylene, nylon, starch and starch derivatives, teflon, polystyrene, polypropylene, talc, and mixtures thereof. Various talc-type particulates are suitable including silicate powders, corn starch, modified corn starch, metallic stearates, and mixtures thereof. Preferred are starch derivatives such as aluminum starch octenylsuccinate which is commercially available from National Starch Corporation.

The invention will be further described in connection with the following examples which are set forth for the purpose of illustration only.

EXAMPLE 1

A soft solid antiperspirant was made as follows:

| | w/w % |
|---|---|
| Cyclomethicone | 25.00 |
| Al/Zr tetrachlorohydrex gly | 24.00 |
| Geahlene* | 19.00 |
| Aluminum starch octenylsuccinate | 18.40 |
| Stearyl alcohol | 5.70 |
| Hydrogenated castor oil | 3.70 |
| Polyethylene | 2.5 |
| Silica | 0.40 |
| Fragrance | 0.50 |
| PEG-20 | 0.15 |
| PEG-25 propylene glycol stearate | 0.15 |
| Water | 0.50 |

EXAMPLE 2

A solid antiperspirant composition was made as follows:

| | w/w % | |
|---|---|---|
| Cyclomethicone | 26.70 | 25.00 |
| Al/Zr tetrachlorohydrex gly | 25.00 | 24.00 |
| Geahlene* | 10.00 | 19.00 |
| Aluminum starch octenylsuccinate | 15.00 | 18.40 |
| Stearyl alcohol | 9.00 | 5.70 |
| Hydrogenated castor oil | 4.00 | 3.70 |
| Polyethylene (6 microns) | 1.00 | 2.50 |
| Silica | 0.25 | 0.40 |
| PEG-20 | 0.15 | 0.15 |
| PEG-25 propylene glycol stearate | 0.40 | 0.15 |
| Hydrogenated polyisobutene | 3.00 | |
| Octyldodecanol | 1.00 | |
| Talc | 4.00 | |
| Propyl paraben | | |
| Fragrance | | 0.50 |

EXAMPLE 3

Deodorant composition in accordance with the invention were made as follows:

| | w/w % Solid | Soft Solid |
|---|---|---|
| Cyclomethicone | 27.00 | 24.00 |
| Geahlene* | 10.00 | 20.00 |
| Aluminum starch octenylsuccinate | 39.20 | 39.05 |
| Stearyl alcohol | 9.30 | 6.30 |
| Hydrogenated castor oil | 4.00 | 4.00 |
| Polyethylene (6 microns) | 1.00 | 2.00 |
| Silica | 0.25 | 0.40 |
| PEG-20 | 0.20 | 0.20 |
| PEG-25 propylene glycol stearate | 4.00 | — |
| Hydrogenated polyisobutene | 1.00 | — |
| Octyl dodecanol | 1.00 | — |
| Talc | 3.00 | 3.00 |
| Propyl paraben | 0.05 | 0.05 |
| Deodorant (FARNESOL) | 0.30 | 0.30 |

*mineral oil and hydrogenated butylene/ethylene/styrene copolymer and hydrogenated ethylene/propylene/styrene copolymer.

We claim:

1. A cosmetic stick composition comprising, by weight of the total composition:
   a) 24–60% of a volatile silicone which is a linear or cyclic volatile polydimethylsiloxane,
   b) 3–25% of a solidifying agent which is a wax,
   c) 10–40% of a gel composition comprised of a a mixture of mineral oil and hydrogenated butylene/ethylene/styrene copolymer and hydrogenated ethylene/propylene/styrene copolymer, and
   d) 10–45% of inert particulate materials which are not antiperspirant salts.

2. The composition of claim 1 wherein the gel composition comprises, by weight of the gel composition, 80–99% mineral oil, and 1–20% of a mixture of mineral oil and hydrogenated butylene/ethylene/styrene copolymer and hydrogenated ethylene/propylene/styrene copolymer.

3. The composition of claim 1 further comprising 5–35% by weight of the total composition of an astringent antiperspirant salt.

4. The composition of claim 3 wherein the inert particulate material has a particle size of 15 to 300 microns.

5. The composition of claim 4 wherein the volatile silicone is cyclomethicone.

6. The composition of claim 5 comprising:

24–50% cyclomethicone,

3–15% wax,

15–30% of a gel composition comprising, by weight of the total gel composition, 80–99% mineral oil, and 1–20% of a mixture of hydrogenated butylene/ethylene/styrene copolymer and hydrogenated ethylene/propylene/styrene copolymer, 10–40% of inert particulate materials which are not antiperspirant salts, and 10–30% of an astringent antiperspirant salt.

7. The composition of claim 6 wherein the wax is hydrogenated castor oil, a fatty alcohol, or mixtures thereof.

8. The composition of claim 6 wherein the inert particulate materials are polyethylene, starch, talc, and mixtures thereof.

9. The composition of claim 6 wherein the astringent antiperspirant salt is aluminum/zirconium tetrachlorohydrex gly.

10. The composition of claim 1 further comprising 0.1–5% of a deodorant active compound.

11. The composition of claim 10 wherein the inert particulate material has a particle size of 15 to 300 microns.

12. The composition of claim 10 wherein the volatile silicone is cyclomethicone.

13. The composition of claim 10 comprising:

24–50% cyclomethicone,

3–15% wax,

15–30% of gel composition comprising, by weight of the gel composition, 80–99% mineral oil, and 1–20% of a mixture of hydrogenated butylene/ethylene/styrene copolymer and hydrogenated ethylene/propylene/styrene copolymer, 10–40% inert particulate materials, and 0.1–2% of a deodorant active compound.

14. The composition of claim 13 wherein the wax a fatty alcohol, hydrogenated castor oil, or mixtures thereof.

15. The composition of claim 11 wherein the deodorant active is 3,7,11-trimethyldodeca-2,6,10-trienol.

16. The composition of claim 12 wherein the inert particulate materials are polyethylene, talc, starch, or mixtures thereof.

* * * * *